(12) United States Patent
Ohshiro et al.

(10) Patent No.: US 8,426,125 B2
(45) Date of Patent: Apr. 23, 2013

(54) METHOD OF PRETREATING SPECIMEN AND IMMUNOASSAY USING THE SAME

(75) Inventors: Kyouichi Ohshiro, Kyoto (JP); Kazuhiro Ohmiya, Kyoto (JP); Naoko Izui, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 17 days.

(21) Appl. No.: 12/949,446

(22) Filed: Nov. 18, 2010

(65) Prior Publication Data

US 2011/0065099 A1 Mar. 17, 2011

Related U.S. Application Data

(62) Division of application No. 11/792,990, filed as application No. PCT/JP2005/022883 on Dec. 13, 2005, now abandoned.

(30) Foreign Application Priority Data

Dec. 14, 2004 (JP) ................................ 2004-361828

(51) Int. Cl.
*C12Q 1/70* (2006.01)
*C12Q 1/00* (2006.01)

(52) U.S. Cl.
USPC .............................................. 435/5; 435/7.1

(58) Field of Classification Search .................. None
See application file for complete search history.

(56) References Cited

U.S. PATENT DOCUMENTS

| 4,355,102 | A | 10/1982 | Quash |
| 4,663,277 | A | 5/1987 | Wang |
| 5,122,449 | A | * | 6/1992 | Gilbert et al. ...................... 435/5 |
| 2004/0175695 | A1 | 9/2004 | Debad et al. |

FOREIGN PATENT DOCUMENTS

| EP | 1 494 030 | 1/2005 |
| JP | 55-30656 | 3/1980 |
| JP | 55-141198 | 11/1980 |
| JP | 2-211894 | 8/1990 |
| JP | 10-267929 | 10/1998 |
| JP | 2002-62299 | 2/2002 |
| JP | 2004-69341 | 3/2004 |
| JP | 2004-245831 | 9/2004 |
| JP | 2005-164496 | 6/2005 |
| WO | 91/06559 | 5/1991 |
| WO | 99/31280 | 6/1999 |

OTHER PUBLICATIONS

Nakamura et al. Internal Medicine vol. 42 pp. 806-811, 2003.*
Montalto 2003 American Family Physician vol. 67, pp. 111-118.*
Hoyle et al., J of Hyg. (Cambridge 1971) vol. 69, pp. 461-469.*
Covalciuc et al., "Comparison of four clinical specimen types for detection of influenza A and B viruses by optical immunoassay (FLU OIA test) and cell culture methods," J. Clin. Microbiol., 1999, 37(12), pp. 3971-3974.
M. Hara, "Comparison of Two Rapid Diagnostic Kits Using Immunochromatography for Detection of Influenza A Viruses", The Journal of the Japan Pediatric Society, vol. 108, No. 3, pp. 406-411 (200) with is English Abstract.
M. Yamazaki, et al., "Evaluation of Flow-through Immunoassay for Rapid Detection of Influenza A and B Viruses", The Journal of the Japanese Association for Infectious Diseases, vol. 78, No. 9, pp. 865-871 (2004) with its English abstract.
N. Kubo, et al., "Evaluation of an immunochromatography Test Kit for Rapid Diagnosis of Influenza", The Journal of the Japanese Association for Infectious Diseases, vol. 77, No. 12, pp. 1007-1014 (2003) with its English abstract.
N. Hagiwara, et al., "Experience of using rapid diagnostic kit of influenza (Capiria Flu A, B) on nasal aspirate specimens", The Japanese Journal of Medical Technology, vol. 52, No. 2, pp. 141-144 (2003).
Gavin, et al., "Review of Rapid Diagnostic Tests for Influenza", Clinical and Applied Immunology Reviews 4 (2003) 151-172 (XP-002503371).
Yolken, et al., "Fluorometric Assay for Measurement of Viral Neuraminidase—Application to the Rapid Detection of Influenza Virus in Nasal Wash Specimens", The Journal of Infectious Diseases, vol. 142, No. 4. Oct. 1980, pp. 516-523 (XP002918039).
Sugimura, et al., "The Susceptibility of Culture Cells to Avian Influenza Virues", J. Vet. Med. Sci., vol. 62, No. 6, 2000, pp. 659-660.
Nakamura, et al.. "A Large Outbreak of Legionnaires' Disease Due to an Inadequate Circulating and Filtration System for Bath Water—Epidemiologic Manifestations-", Internal Medicine, vol. 42, No. 9, 2003, pp. 806-811.
Montalto, et al., "An Office-Based Approach to Influenza: Clinical Diagnosis and Laboratory Testing", American Family Physician, vol. 67, No. 1, 2003, pp. 111-118.

* cited by examiner

*Primary Examiner* — Mary E Mosher
*Assistant Examiner* — Myron Hill
(74) *Attorney, Agent, or Firm* — Morgan, Lewis & Bockius LLP

(57) ABSTRACT

The present invention provides a method of pretreating a specimen, which allows measurement according to an immunoassay to be carried out on a specimen from nasal secretion while preventing non-specific reactions. According to this method, the specimen from nasal secretion is treated with a protease beforehand and then an immunoassay is performed. As the protease, it is preferable to use semi-alkaline protease (EC 3.4.21.63). Furthermore, it is preferable that a substance to be pretreated by the pretreatment method according to the present invention is an influenza virus contained in the specimen from nasal secretion. The immunoassay preferably is an immunoagglutination assay. Examples of the immunoagglutination assay include a turbidimetric immunoassay, a latex turbidimetric immunoassay, and a latex agglutination assay that is performed on a slide glass.

11 Claims, No Drawings

METHOD OF PRETREATING SPECIMEN AND IMMUNOASSAY USING THE SAME

CROSS-REFERENCE TO RELATED APPLICATIONS

This application is a Division of application Ser. No. 11/792,990, filed Jun. 13, 2007, now abandoned, which is a U.S. National Stage application based on International Application No. PCT/JP2005/022883 filed Dec. 13, 2005, which applications are incorporated herein by reference.

TECHNICAL FIELD

The present invention relates to a method of pretreating a specimen and an immunoassay using this method.

BACKGROUND ART

Immunoassays utilizing an antigen-antibody reaction can detect a component or a substance present in a specimen or a sample with high sensitivity. Thus, in the field of clinical tests, such immunoassays have been used for testing various kinds of specimens and the like, such as blood (plasma, serum, whole blood), urine, cerebrospinal fluid, and feces. Examples of the immunoassay utilizing an antigen-antibody reaction include various kinds of assays, such as an enzyme immunoassay (EIA), a fluorescence immunoassay (FIA), a chemiluminescent immunoassay (CLIA), an immunochromatography assay, a turbidimetric immunoassay (TIM, and a latex turbidimetric immunoassay (LTIA).

Among these, the turbidimetric immunoassay, the latex turbidimetric immunoassay, and a latex agglutination assay that is performed on a slide glass (hereinafter, these three assays may be referred to generically as "immunoagglutination assays") are called homogeneous immunoassays, because they operate without performing B/F (Bound/Free) separation for separating antigens and unreacted antibodies. The immunoagglutination assays have been applied to a large number of items in clinical tests, e.g., CRP (C-reactive protein), ASO (antistreptolysin O), RF (rheumatoid factors), microalbumin in urine, and elastase, because they are excellent in simplicity and rapidity of operation.

Specimens to be subjected to these immunoagglutination assays generally are blood (serum, plasma, whole blood), urine, cervical mucus, etc. On the other hand, items to be measured by testing specimens from nasal secretion, collected as nasal swab, nasal aspirate, nasal wash, etc., include those used for determining whether the patient is infected with respiratory infectious diseases, such as influenza viruses and RS viruses. However, these items are all measured by an immunochromatography assay or an EIA using a membrane filter. A measurement method that operates using an immunoagglutination assay and is applicable to specimens from nasal secretion has not yet been in practical use (see Non-Patent Documents 1 to 4, for example).

Many specimens from nasal secretion have some degree of viscosity, although the viscosity varies from one specimen to another. As can be seen from this fact, the specimens from nasal secretion contain, in addition to a target analyte, a very high content of macromolecular substances such as glycoproteins. It has been known that, in the immunochromatography assay or the EIA using a membrane filter, nonspecific reactions may be caused by any of the substances that are present with the analyte in the specimen to bring about a false test result, although the substance causing the nonspecific reactions is not yet identified. When the test result incorrectly shows false positive, it causes a delay in identifying the actual cause of the disease. Moreover, it may lead to an inappropriate treatment that may aggravate the symptoms of the disease. On this account, the specimens from nasal secretion are subjected to measurement after lowering the viscosity thereof by adding a detergent or after removing solid components (the substances present with the analyte) contained therein with a filter paper or a filter, for example. However, still, a large number of false positive results are caused by the nonspecific reactions.

The inventors of the present invention conducted a keen study in order to realize the measurement on a specimen from nasal secretion by a simple immunoagglutination assay, as had already been realized by the immunochromatography assay or the EIA using a membrane filter. The inventors found out that, when the specimen was pretreated merely by adding a detergent or by removing solid components beforehand, a large number of non-specific reactions still were caused so that the specimen that was supposed to give a negative result gave a positive result, i.e., a false positive result.

Non-Patent Document 1: The Journal of the Japan Pediatric Society, Vol. 108, No. 3, pp 406-411 (2004)

Non-Patent Document 2: The Journal of the Japanese Association for Infectious Diseases, Vol. 78, No. 9, pp 865-871 (2004)

Non-Patent Document 3: The Journal of the Japanese Association for Infectious Diseases, Vol. 77, No. 12, pp 1007-1014 (2003)

Non-Patent Document 4: The Japanese Journal of Medical Technology, Vol. 52, No. 2, pp 141-144 (2003)

DISCLOSURE OF INVENTION

Problem to be Solved by the Invention

Therefore, with the foregoing in mind, it is an object of the present invention to provide a method of pretreating a specimen, which allows measurement according to an immunoassay to be carried out on a specimen from nasal secretion while preventing non-specific reactions, and also provide an immunoassay using this method.

Means for Solving Problem

In order to achieve the above object, the present invention provides a method of pretreating a specimen for an immunoassay, wherein the specimen is obtained from nasal secretion, and the specimen is treated with a protease before performing the immunoassay.

Furthermore, the present invention provides an immunoassay utilizing an antigen-antibody reaction, wherein a specimen is obtained from nasal secretion, and the specimen is pretreated by the pretreatment method according to the present invention and then the antigen-antibody reaction is carried out.

Effects of the Invention

As described above, by treating a specimen from nasal secretion with a protease beforehand, it becomes possible to carry out the measurement according to an immunoassay on the specimen from nasal secretion while preventing non-specific reactions. As a result, the present invention can realize the measurement on a specimen from nasal secretion, which is excellent in simplicity and rapidity in operation.

DESCRIPTION OF THE INVENTION

In the following, the present invention will be described in detail.

In the present invention, the immunoassay is not particularly limited, and can be, for example, an assay for measuring the concentration of an analyte in the specimen by causing an antigen-antibody reaction between the analyte and an immunologic substance that is carried by an insoluble carrier and immunoreactive with the analyte and measuring a degree to which agglutination of the insoluble carrier has caused by the antigen-antibody reaction (this assay is a so-called "immunoagglutination assay"). The method of pretreating a specimen according to the present invention preferably is applied to this immunoagglutination assay.

The protease to be used in the present invention is not particularly limited, and can be an animal protease, a plant protease, and a protease from a microorganism of the genus *Aspergillus*, the genus *Bacillus*, the genus *Streptomyces*, the genus *Rhizopus*, the genus *Penicillium*, or the like. Specific enzyme names thereof are, for example, a semi-alkaline protease, trypsin, chymotrypsin, elastase, subtilisin, proteinase K, pronase, papain, bromelain, etc. These proteases may be used alone or in a combination of at least two kinds thereof.

As the specimen from nasal secretion, specimens obtained as nasal swab, nasal aspirate, and nasal wash can be used, for example.

The present invention can be used suitably when the analyte is an influenza virus. In this case, according to the present invention, the amount of the virus can be measured quantitatively by quantitating the degree to which agglutination of the insoluble carrier has occurred. By considering the result of this measurement in combination with the clinical symptoms, the following can be known. That is, when the specimen contains a large amount of virus, it is possible to estimate the degree of seriousness of the disease of the patient to a certain extent and also to expect that the patient is highly infectious to people around him. Furthermore, when the amount of virus decreases with the passage of time after the onset of the disease, it can be expected more easily that the disease is in its end stage, which helps to decide the therapeutic strategy and to make an explanation to the patient.

The treatment of the specimen from nasal secretion with a protease is not particularly limited as long as the protease is used. For example, as in the case of measuring the enzyme activity of a protease, this protease treatment can be carried out under general conditions within a pH range where the enzyme activity of the protease is effective. When the protease is a semi-alkaline protease, the protease treatment is carried out by, for example, dissolving the enzyme in a 50 mM CHES (N-Cyclohexyl-2-aminoethanesulfonic acid) buffer solution (pH 9.8, containing 1 wt % n-Octanoyl-N-methylglucamide, 0.1 wt % EDTA.2Na, 0.9 wt % NaCl, and 0.09 wt % sodium azide) to prepare a specimen extraction solution and then reacting the specimen extraction solution with the specimen from nasal secretion. Note here that the buffer solution used for preparing the specimen extraction solution is not limited to the CHES buffer solution, and a phosphate buffer solution, a Tris-HCl buffer solution, a CAPS (N-Cyclohexyl-3-aminopropanesulfonic acid) buffer solution, etc. also can be used preferably, for example. It is preferable that the pH of the buffer solution is in the range from 5 to 11, for example. When the buffer solution has a pH in this range, the type of the buffer contained therein, for example, is not particularly limited. When the protease is trypsin, chymotrypsin, elastase, or subtilisin, the protease treatment can be carried out by, for example, dissolving the enzyme in a 50 mM Tris-HCl buffer solution (pH: 8.4, containing 1 wt % n-Octanoyl-N-methylglucamide, 0.03 wt % $CaCl_2$, 0.9 wt % NaCl, and 0.09 wt % sodium azide) and then reacting the resultant solution with the specimen from nasal secretion.

Among these preferable proteases, semi-alkaline protease (EC 3.4.21.63), for example, can be used particularly preferably as the protease in the present invention, because it is least susceptible to the influence of the specimen and particularly compatible with the insoluble carrier.

In the present invention, it is preferable that the immunoassay is an assay utilizing an immunoagglutination assay in which insoluble carriers are used, as described above. The insoluble carriers are not particularly limited, and can be insoluble carrier particles. As the insoluble carrier particles, latex particles made of polystyrene are used commonly, for example. However, the insoluble carrier particles are not limited to those made of polystyrene, and it is also possible to use particles that can be sensitized with antibodies or antigens, such as particles made of polypropylene, particles made of polyethylene, gelatin particles, and metal colloids. The bonding between the particles and the antigens or antibodies can be achieved by, for example, a physical adsorption method utilizing physical adsorptive power. Besides this, the bonding between the particles and the antigens or antibodies can be achieved by, for example, a chemical bonding method by which carboxyl groups on the particles are covalently bound to amino groups of the antigens or antibodies. The degree to which agglutination has occurred can be detected by, for example, using an automatically controlled optical measuring device, such as a spectrophotometer for measuring turbidity. Alternatively, it can be detected by visually checking the presence or absence of agglutination on a slide glass or the like.

In the present invention, when the analyte is an influenza virus, it is preferable to identify whether the virus is an influenza A virus or an influenza B virus. In this case, it is preferable to use an antibody that is specific to a nucleoprotein of the influenza virus, for example. The antigenicity of hemagglutinin or the like as an influenza virus surface protein changes successively. Thus, the use of a certain type of anti-hemagglutinin antibody brings about a disadvantage in that the antibody may not react with a target virus because the reactivity of the antibody varies depending on the prevalent subtype of the virus. In contrast, a nucleoprotein maintains an antigenicity that serves as a basis on which an influenza virus is classified into the type A or type B. Thus, an antibody against the nucleoprotein exhibits a constant reactivity regardless of the subtype of the virus and thus can be used suitably to identify whether the target virus is an influenza A virus or an influenza B virus.

Since the nucleoprotein is localized inside the envelope, which is composed of a lipid bilayer, of a virus particle and is not present on the virus surface, it is necessary to extract the nucleoprotein in some way. Examples of the method of extracting the nucleoprotein include a treatment using ultrasonic waves, physical destruction of virus particles by repeating freezing and thawing, and a chemical treatment using a detergent or the like. In the chemical treatment, the nucleoprotein generally is extracted using, as an extractant, a non-ionic detergent such as Tween 20 (trade name, a common name of which is "Polyoxyethylene Sorbitan Monolaurate"). In conventional methods such as an EIA and an immunochromatography assay, the extraction of an antigen is performed using Tween 20 as a detergent. However, when Tween 20 is used in a latex turbidimetric immunoassay as in the conventional methods, the reactivity with the antigen decreases significantly. In such a case, n-Octanoyl-N-methylglucamide (trade name: MEGA-8) preferably is used as a detergent, because it slightly influences the reactivity in the latex turbidimetric immunoassay and also exhibits an extracting effect.

In the following, the present invention will be described by way of examples. It is to be noted, however, that the present invention is by no means limited to the following examples.

Example 1

Experiment 1

Preparation of Latex Sensitized with Anti-Influenza A Antibody 0.5 ml of an antibody solution (in 50 mM phosphate buffer solution, pH 7.4) prepared so as to contain a 0.8 mg/ml anti-influenza A mouse monoclonal antibody was mixed with 0.5 ml of 1% (w/v) polystyrene latex particles (Sekisui Chemical Co., Ltd., average particle diameter: 0.5 μm). The resultant mixture was incubated at 37° C. for 1 hour, thus sensitizing the latex particles with the antibody. To this mixture, BSA (Sigma, bovine serum albumin) was added so that its concentration was 1 wt %. Thereafter, the resultant mixture was incubated at 37° C. for 1 hour to perform blocking. The antibody-sensitized latex particles that had been subjected to the blocking were washed with a 50 mM phosphate buffer solution (pH 7.4) and then dispersed in a latex dispersion buffer solution (in 50 mM Tris-HCl buffer solution, pH 8.4, 0.1 wt % BSA, 0.1 wt % NaN$_3$) so that its concentration was 0.1% (w/v). Thus, an anti-influenza A antibody-sensitized latex test solution was obtained.

Experiment 2

Preparation of Latex Sensitized with Anti-Influenza B Antibody 0.5 ml of an antibody solution (in 50 mM phosphate buffer solution, pH 7.4) prepared so as to contain a 0.6 mg/ml anti-influenza B mouse monoclonal antibody was mixed with 0.5 ml of 1% (w/v) polystyrene latex particles (Sekisui Chemical Co., Ltd., average particle diameter: 0.6 μm). The resultant mixture was incubated at 37° C. for 1 hour, thus sensitizing the latex particles with the antibody. The operation after the blocking was performed in the same manner as in Experiment 1. Thus, an anti-influenza B antibody-sensitized latex test solution was obtained.

A series of experiments described below were conducted using, as a protease, a semi-alkaline protease.

Experiment 3

Preparation of Specimen Extraction Solution 0.4 mg of semi-alkaline protease (*Aspergillus melleus*, Semi-Alkaline Proteinase available from Amano Enzyme Inc.) was dissolved in 1 ml of a 50 mM CHES (N-Cyclohexyl-2-aminoethanesulfonic acid) buffer solution (pH 9.8) containing 1 wt % n-Octanoyl-N-methylglucamide (trade name: MEGA-8, hereinafter the same), 0.1 wt % EDTA.2Na, 0.9 wt % NaCl, and 0.09 wt % sodium azide. Thus, a specimen extraction solution A was obtained.

Furthermore, 0.4 mg of semi-alkaline protease (*Aspergillus melleus*, Semi-Alkaline Proteinase available from Amano Enzyme Inc.) was dissolved in 1 ml of a 50 mM Tris-HCl buffer solution (pH 8.4) containing 1 wt % n-Octanoyl-N-methylglucamide, 0.5 wt % BSA, 0.9 wt % NaCl, and 0.1 wt % EDTA.2Na. Thus, a specimen extraction solution B was obtained.

Experiment 4

Measurement on Influenza A Antigen Standard Solution According to Latex Turbidimetric Immunoassay Purified influenza A virus A/Kiev/301/94 (H3N2) as an antigen was diluted with a specimen diluent (in PBS containing 1 wt % BSA and 0.1 wt % sodium azide, pH 7.4) so as to achieve predetermined virus concentrations (4 μg/ml and 20 μg/ml). Thus, two types of virus solutions were prepared. Furthermore, immediately before conducting a measurement, the virus solutions with the respective virus concentrations were diluted 10-fold with the specimen extraction solution B (in 50 mM Tris-HCl buffer solution containing 0.4 mg/ml of the semi-alkaline protease, 1 wt % n-Octanoyl-N-methylglucamide, 0.5 wt % BSA, 0.9 wt % NaCl, and 0.1 wt % EDTA.2Na, pH 8.4). The resultant solutions were used as specimens in the measurement according to a latex turbidimetric immunoassay. As a specimen with the virus concentration of 0%, a solution obtained by diluting the above-described specimen diluent 10-fold with the specimen extraction solution B was used.

As a reaction buffer solution, a 200 mM Tris-HCl (pH8.4) buffer solution containing 2.1 wt % polyethylene glycol 20000 (Nacalai Tesque, Inc.), 1 wt % BSA, 0.9 wt % NaCl, 0.1 wt % EDTA.2Na, and 0.1 wt % sodium azide was used. For the absorbance measurement, an immunoreaction measuring system "SPOTCHEM-IM" (ARKRAY, Inc.) was used. The respective reagents and each of the specimens were mixed together in a cuvette in the following proportions. The mixture was treated at 37° C. for 5 minutes, and the change in absorbance in 5 minutes was measured (measurement wavelength: 660 nm). The results obtained are shown in Table 1 below.

| | |
|---|---|
| S (specimen): | 28 μl |
| R1 (reaction buffer solution): | 56 μl |
| R2 (antibody-sensitized latex test solution): | 56 μl |

TABLE 1

| | Concentration of influenza A virus antigen (μg/ml) | | |
|---|---|---|---|
| | 0 | 4 | 20 |
| Absorbance change for 5 min (660 nm) | −0.0039 | 0.0344 | 0.1043 |

As can be seen from Table 1, the absorbance change increased (i.e., the reaction proceeded) proportionally to the influenza A virus concentration. This demonstrates that, by treating the specimen with the specimen extraction solution containing the semi-alkaline protease, it is possible to measure the amount of influenza A virus quantitatively by the latex turbidimetric immunoassay.

Experiment 5

Measurement on Influenza B Antigen Standard Solution According to Latex Turbidimetric Immunoassay Purified influenza B virus B/Victoria/504/00 as an antigen was diluted with a specimen diluent (in PBS containing 1 wt % BSA and 0.1 wt % sodium azide, pH 7.4) so as to achieve predetermined virus concentrations (1 μg/ml and 5 μg/ml). Thus, two types of virus solutions were prepared. Furthermore, immediately before conducting a measurement, the virus solutions with the respective virus concentrations were diluted 10-fold with the specimen extraction solution B (in 50 mM Tris-HCl buffer solution containing 0.4 mg/ml of the semi-alkaline protease, 1 wt % n-Octanoyl-N-methylglucamide, 0.5 wt % BSA, 0.9 wt % NaCl, and 0.1 wt % EDTA.2Na, pH 8.4). The resultant solutions were used as specimens in the measurement according to a latex turbidimetric immunoassay. As a specimen with the virus concentration of 0%, a solution obtained by diluting the above-described specimen diluent 10-fold with the specimen extraction solution B was used.

As a reaction buffer solution, a 200 mM Tris-HCl (pH8.4) buffer solution containing 1.95 wt % polyethylene glycol 20000 (Nacalai Tesque, Inc.), 1 wt % BSA, 0.9 wt % NaCl, 0.1% EDTA.2Na, and 0.1 wt % sodium azide was used. For the absorbance measurement, an immunoreaction measuring system "SPOTCHEM-IM" (ARKRAY, Inc.) was used. The respective reagents and each of the specimens were mixed together in a cuvette in the following proportions. The mixture was treated at 37° C. for 5 minutes, and the change in absorbance for 5 minutes was measured (measurement wavelength: 730 nm). The results obtained are shown in Table 2 below.

| | |
|---|---|
| S (specimen): | 28 µl |
| R1 (reaction buffer solution): | 56 µl |
| R2 (antibody-sensitized latex test solution): | 56 µl |

TABLE 2

| | Concentration of influenza B virus antigen (µg/ml) | | |
|---|---|---|---|
| | 0 | 1 | 5 |
| Absorbance change for 5 min (730 nm) | 0.0003 | 0.0193 | 0.0642 |

As can be seen from Table 2, the absorbance change increased (i.e., the reaction proceeded) proportionally to the influenza B virus concentration. This demonstrates that, by treating the specimen with the specimen extraction solution containing the semi-alkaline protease, it is possible to measure the amount of influenza B virus quantitatively by the latex turbidimetric immunoassay.

Experiment 6

Measurement on Influenza A-Negative Specimens

Nasal aspirates were collected from humans who obviously were judged as not being infected with influenza from their symptoms. Among the thus-collected nasal aspirates, those proved as influenza A-negative using a commercially available influenza virus detection kit (Nippon Becton Dickinson Co, Ltd., trade name: Capilia FluA/B), which operates based on an immunochromatography assay, were used as specimens (14 specimens), and these specimens were subjected to the influenza A virus measurement. The measurement was carried out basically in the same manner as in Experiment 4, except that the nasal aspirate put on a cotton swab was suspended in 1 ml of a specimen extraction solution. The specimen extraction solution used in the present experiment had the same composition as the specimen extraction solution B used in Experiment 4 except for the protease. In the present experiment, an extraction solution B-1 containing no semi-alkaline protease and an extraction solution B-2 containing 0.4 mg/ml of the semi-alkaline protease were used. The results obtained using these extraction solutions B-1 and B-2 were compared with each other so as to examine the nonspecific reaction-inhibiting effect of the semi-alkaline protease. In the qualitative judgment of the specimen, the specimen was judged as positive (+) when the absorbance change was 0.0050 or more and as negative (−) when the absorbance change was less than 0.0050. These results are shown in Table 3 below. Note here that the comparative example refers to the case where the extraction solution B-1 was used, and the example refers to the case where the extraction solution B-2 was used.

TABLE 3

| Sample number # | Comparative example Extraction solution B-1 | | Example Extraction solution B-2 | |
|---|---|---|---|---|
| | Absorbance change | Result | Absorbance change | Result |
| 1 | 0.0044 | − | −0.0037 | − |
| 2 | 0.0416 | + | −0.0002 | − |
| 3 | 0.0039 | − | −0.0060 | − |
| 4 | 0.0323 | + | −0.0043 | − |
| 5 | 0.0109 | + | −0.0052 | − |
| 6 | 0.0411 | + | −0.0001 | − |
| 7 | 0.0593 | + | −0.0022 | − |
| 8 | 0.0455 | + | −0.0084 | − |
| 9 | 0.0382 | + | −0.0013 | − |
| 10 | 0.0254 | + | −0.0101 | − |
| 11 | 0.0153 | + | −0.0064 | − |
| 12 | 0.0260 | + | −0.0086 | − |
| 13 | 0.0227 | + | −0.0083 | − |
| 14 | 0.0209 | + | −0.0042 | − |

As can be seen from Table 3, when the specimens were treated with the extraction solution B-1 containing no semi-alkaline protease in the influenza A virus measurement according to the latex turbidimetric immunoassay, non-specific agglutination reactions occurred to cause a false positive result in 12 specimens out of the 14 specimens. On the other hand, when the specimens were treated with the extraction solution B-2 containing the semi-alkaline protease, the 14 specimens all exhibited a negative result as they were supposed to.

Experiment 7

Measurement on Influenza B-Negative Specimens

Nasal aspirates were collected from humans who obviously were judged as not being infected with influenza from their symptoms. Among the thus-collected nasal aspirates, those proved as influenza B-negative using a commercially available influenza virus detection kit (Nippon Becton Dickinson Co, Ltd., trade name: Capilia FluA/B), which operates based on an immunochromatography assay, were used as specimens (eight specimens), and these specimens were subjected to the influenza B virus measurement. The measurement was carried out basically in the same manner as in Experiment 5, except that the nasal aspirate put on a cotton swab was suspended in 1 ml of a specimen extraction solution. The specimen extraction solution used in the present experiment had the same composition as the specimen extraction solution B used in Experiment 4 except for the protease. In the present experiment, an extraction solution B-1 containing no semi-alkaline protease and an extraction solution B-2 containing 0.4 mg/ml of the semi-alkaline protease were used. The results obtained using these extraction solutions B-1 and B-2 were compared with each other so as to examine the nonspecific reaction-inhibiting effect of the semi-alkaline protease. In the qualitative judgment of the specimen, the specimen was judged as positive (+) when the absorbance change was 0.0050 or more and as negative (−) when the absorbance change was less than 0.0050. These results are shown in Table 4 below. Note here that the specimens #15 to #19 were influenza A and B negative, while the three specimens from #20 to #22 were influenza A positive and influenza B negative. Note here that the comparative example refers to the case where the extraction solution B-1 was used, and the example refers to the case where the extraction solution B-2 was used.

TABLE 4

| Sample number # | Comparative example Extraction solution B-1 | | Example Extraction solution B-2 | |
| --- | --- | --- | --- | --- |
| | Absorbance change | Result | Absorbance change | Result |
| 15 | 0.0028 | − | −0.0058 | − |
| 16 | 0.0203 | + | −0.0018 | − |
| 17 | 0.0319 | + | −0.0032 | − |
| 18 | 0.0274 | + | −0.0034 | − |
| 19 | 0.0328 | + | −0.0043 | − |
| 20 | 0.0651 | + | −0.0033 | − |
| 21 | 0.0298 | + | −0.0018 | − |
| 22 | 0.0241 | + | −0.0040 | − |

As can be seen from Table 4, when the specimens were treated with the extraction solution B-1 containing no semi-alkaline protease in the influenza B virus measurement according to the latex turbidimetric immunoassay, non-specific agglutination reactions occurred to cause a false positive result in seven specimens out of the eight specimens. On the other hand, when the specimens were treated with the extraction solution B-2 containing the semi-alkaline protease, the eight specimens all exhibited a negative result as they were supposed to.

Experiment 8

Correlation Test with Regard to Influenza A Virus

Nasal aspirates collected from 61 patients who were clinically suspected to be influenza infected were used as specimens. These specimens were treated with the specimen extraction solution A containing the semi-alkaline protease (prepared in Experiment 3) according to the present invention and then were subjected to the measurement according to a latex turbidimetric immunoassay. The measurement was carried out in the same manner as in Experiment 6. Using the thus-obtained date regarding the absorbance change, the specimens were subjected to the qualitative judgment as to whether they were positive (+) or negative (−) based on the above-described criteria, and the results were compared with those obtained by a control method. As a control method, a virus isolation culture method using MDCK (Madin-Darby canine kidney) cells was conducted. The correspondence between the results obtained by both methods is shown in Table 5 below.

TABLE 5

| | | Virus isolation culture | | |
| --- | --- | --- | --- | --- |
| | | Positive (+) | Negative (−) | Total |
| Latex turbidimetric immunoassay | Positive (+) | 23 | 5 | 28 |

TABLE 5-continued

| | | Virus isolation culture | | |
| --- | --- | --- | --- | --- |
| | | Positive (+) | Negative (−) | Total |
| (Present invention) | Negative (−) | 4 | 29 | 33 |
| Total | | 27 | 34 | 61 |

As can be seen from Table 5, when the nasal aspirate specimens were pretreated with the specimen extraction solution A containing the semi-alkaline protease and then subjected to the influenza A virus measurement according to the latex turbidimetric immunoassay, the results obtained exhibited favorable correlation with the results obtained by the virus isolation culture method as a control method. This demonstrates that the immunoassay according to the present invention sufficiently can serve as an alternative to the conventional virus isolation culture method.

Experiment 9

Correlation Test with Regard to Influenza B Virus

Nasal aspirates collected from 35 patients who were clinically suspected to be influenza infected were used as specimens. These specimens were treated with the specimen extraction solution A containing the semi-alkaline protease (prepared in Experiment 3) according to the present invention and then were subjected to the measurement according to a latex turbidimetric immunoassay. The measurement was carried out in the same manner as in Experiment 7. Using the thus-obtained date regarding the absorbance change, the specimens were subjected to the qualitative judgment as to whether they were positive (+) or negative (−) based on the above-described criteria, and the results were compared with those obtained by a control method. As a control method, measurement was carried out using a commercially available influenza B virus detection kit (Nippon Becton Dickinson Co, Ltd., trade name: Capilia FluB), which operates based on an immunochromatography assay. The correspondence between the results obtained by both methods is shown in Table 6 below

TABLE 6

| | | Immunochromatography assay | | |
| --- | --- | --- | --- | --- |
| | | Positive (+) | Negative (−) | Total |
| Latex turbidimetric immunoassay (Present invention) | Positive (+) | 11 | 3 | 14 |
| | Negative (−) | 1 | 20 | 21 |
| Total | | 12 | 23 | 35 |

As can be seen from Table 6, when the nasal aspirate specimens were pretreated with the specimen extraction solution A containing the semi-alkaline protease and then subjected to the influenza B virus measurement according to the latex turbidimetric immunoassay, the results obtained exhibited favorable correlation with the results obtained by the immunochromatography assay as a control method. This demonstrates that the immunoassay according to the present invention sufficiently can serve as an alternative to the conventional immunochromatography assay.

INDUSTRIAL APPLICABILITY

As described above, by using a pretreatment method according to the present invention, it becomes possible to carry out an immunoassay of a specimen from nasal secretion while preventing the occurrence of non-specific reactions. Therefore, the pretreatment method according to the present invention is applicable to a wide range of fields including medical science and biology, and is particular useful in the field of clinical tests.

The invention claimed is:

1. A method of using an immunoassay utilizing an antigen-antibody reaction for measuring a concentration of an analyte in a specimen, comprising:
   pretreating a specimen obtained from nasal secretion with a protease wherein the protease is a semi-alkaline protease, and then
   carrying out an antigen-antibody reaction between an analyte in the specimen and an immunologic substance that is carried by an insoluble carrier and is immunoreactive with the analyte and
   measuring the degree to which agglutination of the insoluble carrier has been caused by the antigen-antibody reaction,
wherein the analyte in the specimen is an influenza virus, and wherein the immunologic substance carried by the insoluble carrier is an antibody against the influenza virus.

2. The method according to claim 1, wherein the protease is dissolved in a buffer solution and the pH of the buffer solution is in the range from 5 to 11.

3. The method of claim 1, wherein the semi-alkaline protease is EC 3.4.21.63.

4. The method of claim 1, wherein the insoluble carrier is in the form of particles.

5. The method of claim 4, wherein the particles comprise polystyrene, polypropylene, polyethylene, gelatin or metal colloids.

6. The method of claim 1, wherein the influenza virus is influenza A.

7. The method of claim 1, wherein the influenza virus is influenza B.

8. The method of claim 1, wherein the degree of agglutination is detected by use of an automatically controlled optical measuring device.

9. The method of claim 8, wherein the optical measuring device is a spectrophotometer for measuring turbidity.

10. The method of claim 2, wherein the buffer solution is a CHES (N-Cyclohexyl-2-aminoethanesulfonic acid) buffer solution.

11. The method of claim 2, wherein the buffer solution is selected from the group consisting of a phosphate buffer solution, a Tris-HCl buffer solution and a CAPS (N-Cyclohexyl-3-aminopropanesulfonic acid) buffer solution.

* * * * *